United States Patent
Takada et al.

(10) Patent No.: US 6,474,163 B1
(45) Date of Patent: Nov. 5, 2002

(54) ULTRASONIC FLAW DETECTION METHOD AND INSTRUMENT THEREFOR

(75) Inventors: Hajime Takada; Akira Torao; Ikuo Yarita, all of Chiba (JP)

(73) Assignee: Kawasaki Steel Corporation, Kobe (JP)

(*) Notice: Subject to any disclaimer, the term of this patent is extended or adjusted under 35 U.S.C. 154(b) by 0 days.

(21) Appl. No.: 09/647,554

(22) PCT Filed: Mar. 3, 1999

(86) PCT No.: PCT/JP99/01024

§ 371 (c)(1),
(2), (4) Date: Nov. 1, 2000

(87) PCT Pub. No.: WO00/52460

PCT Pub. Date: Sep. 8, 2000

(51) Int. Cl.[7] .......................... G01N 29/06; G01N 29/10; G01N 29/26
(52) U.S. Cl. .......................... 73/600; 73/602; 73/614; 73/159
(58) Field of Search .......................... 73/597, 598, 599, 73/600, 602, 609, 610, 614, 159, 620, 627

(56) References Cited

U.S. PATENT DOCUMENTS

| | | | | |
|---|---|---|---|---|
| 2,912,853 A | * | 11/1959 | Hanysz | 73/600 |
| 3,953,825 A | * | 4/1976 | Kino et al. | 367/101 |
| 4,018,082 A | * | 4/1977 | Manoliu et al. | 73/600 |
| 4,258,574 A | * | 3/1981 | Hildebrand et al. | 73/625 |
| 4,406,167 A | * | 9/1983 | Maeda | 73/622 |
| 4,491,020 A | * | 1/1985 | Chubachi | 73/606 |
| 4,730,495 A | * | 3/1988 | Green | 73/606 |
| 4,741,212 A | * | 5/1988 | Rehwald | 73/600 |

FOREIGN PATENT DOCUMENTS

| | | | | |
|---|---|---|---|---|
| EP | 1 077 376 A1 | * | 2/2001 | G01N/29/10 |
| JP | 7-253414 | | 10/1995 | |
| JP | 10-078416 A | * | 3/1998 | G01N/29/10 |
| JP | 10-078417 A | * | 3/1998 | G01N/29/22 |
| JP | 10-082768 A | * | 3/1998 | G01N/29/22 |
| JP | 11-051911 A | * | 2/1999 | G01N/29/10 |
| JP | 11-083815 | * | 9/2000 | G01N/29/10 |
| WO | WO 00/52460 | * | 9/2000 | G01N/29/10 |

* cited by examiner

*Primary Examiner*—Daniel S. Larkin
*Assistant Examiner*—Rose M. Miller
(74) *Attorney, Agent, or Firm*—Oliff & Berridge, PLC

(57) ABSTRACT

A method and apparatus for ultrasonic flaw detection of line focus type suitable for detection of flaws in nonmetallic materials included in an object. Ultrasonic transmitter and receiver elements of line focus type are opposed at a distance (L) with an object under test placed between them, and a maximum ultrasonic echo is obtained at a distance $L_p$ expressed by: $L_p = 0.75(FT+FR) - \{(CS/CW)-1\}t$ where FT (mm) is the focal length in the medium of the ultrasonic transmitter element of line focus type, FR (mm) is the focal length in the medium of the ultrasonic receiver element line focus type, CS (m/sec) is the speed of ultrasound in an object under test, CW (m/sec) is the speed of ultrasound in the medium, and t (mm) is the thickness of the object under test.

18 Claims, 6 Drawing Sheets

ULTRASONIC FLAW DETECTION METHOD AND INSTRUMENT THEREFOR

TECHNICAL FIELD

The present invention relates to an ultrasonic flaw detection method and an instrument therefor. The present invention is specifically suitable for detecting internal flaws such as nonmetallic inclusions in a rolled metallic sheet including a steel sheet. By use of the present invention, flaw detection at a time of a linear region with definite width is possible.

BACKGROUND ART

An internal flaw such as microscopic nonmetallic inclusion of approximately 50 µm in diameter in a rolled metallic sheet may cause a crack when the rolled metallic sheet is pressed or drawn. Therefore, it is required for the internal flaw inspection of a rolled metallic sheet to detect an extremely small internal flaw.

Generally, the ultrasonic flaw detection method is most frequently applied to internal flaw inspection of rolled metallic materials. In this method, ultrasonic waves are propagated into rolled metallic materials so as to detect discontinuity in ultrasound propagation caused by the internal flaw. As an applied example of this method, there is a method for flaw inspection of entire volume of the rolled metallic sheet at a transfer line of the rolled metallic sheet. In Japanese Unexamined Patent Publication No. 7-253414, for example, the following ultrasonic flaw detection method and the instrument therefor are proposed. That is, in medium, a line-focused ultrasonic transmitting probe and a linear probe array are arranged face to face with a sheet being inspected (a rolled metallic sheet) between them. A line-focused ultrasonic beam transmitted from the transmitting probe propagates into the sheet being inspected approximately in a perpendicular direction thereto, so that part of ultrasound reflected at an internal flaw in the sheet being inspected will be received by the linear probe array. After the ultrasonic signal which had been received and transformed into the electrical signal was amplified and only the echo from internal flaw was picked up therefrom, any signal greater than a predetermined threshold voltage is detected.

However, in order to detect flaws effectively by use of the above-mentioned ultrasonic flaw detection method and the instrument therefor, the gap length "Ls" (mm) between the line-focused ultrasonic transmitting probe and the linear probe array is required to satisfy the following equation. In this equation, "F" (mm) represents a focal length in medium, of the line-focused ultrasonic transmitting probe, and "t" (mm) denotes a thickness of the sheet being inspected.

$$Ls \leq F - \{(CS/CW)-1\}t+5.5$$

(Provided that: "CS"; ultrasonic velocity (m/sec) in the sheet being inspected, "CW"; ultrasonic velocity (m/sec) in the medium) Accordingly, when a steel sheet of 4.5 mm in thickness is inspected and the focal length in the medium of the line-focused ultrasonic transmitting probe "F"=38 mm, the gap length "Ls" between the transmitting probe and the receiving probe is required to be less than 31 mm.

A problem with this method is that there may be cases that the sheet being inspected in on-line inspection has a wavy shape in its edge or side portion. When the sheet having such a wavy shape is passed through between the transmitting probe and the receiving probe with the gap length of less than 31 mm, it may frequently hit the housing of the probe to be scratched thereon. The impact of the hit on the probe shortens probe's useful life. In the worst case, the probe is broken.

It is an object of the present invention to provide an ultrasonic flaw detection method and an instrument therefor, having such an enough gap length between the transmitting probe and the receiving probe to be passed through by the sheet being inspected having a wavy shape that the sheet will not hit the probes and moreover being reliably detectable the internal flaw such as a microscopic nonmetallic inclusion.

DISCLOSURE OF INVENTION

The inventors have ardently studied conventional ultrasonic flaw detection methods, so that the present invention has been made based on a new knowledge that the gap length between a line-focused ultrasonic transmitting probe and a line-focused ultrasonic receiving probe is determined by the height of a flaw echo which is a function of a focal length in a coupling medium of the line-focused ultrasonic beam of the line-focused ultrasonic transmitting probe and a focal length in a coupling medium of the line-focused receiving beam of the line-focused ultrasonic receiving probe, and so forth. That is, summarized configurations of the present invention are as follows.

(1) An ultrasonic flaw detection method comprising the steps of: transmitting ultrasonic waves into the sheet being inspected approximately in a perpendicular direction to the sheet through a coupling medium with a line-focused ultrasonic transmitter; receiving ultrasonic waves reflected at an internal flaw through the coupling medium with a line-focused ultrasonic receiver; amplifying the received ultrasonic signals which have been transformed into electrical signals; picking up amplified signals of the echo from the internal flaw; and detecting the flaw by detecting the signal more than a predetermined threshold amplitude, wherein the transmitter and the receiver are arranged face to face with the sheet being inspected between them, and wherein the gap length (L) between the transmitter and the receiver is near the minimum value (Lp) in which the height (f(L))of the echo from the internal flaw takes the maximum value.

(2) The method in the above (1), wherein Lp is determined by a focal length (FT) of the line-focused ultrasonic transmitter in the coupling medium, a focal length (FR) of the line-focused ultrasonic receiver in the coupling medium, the velocity (CS) of ultrasonic waves in the sheet being inspected, the velocity (CW) of ultrasonic waves in the coupling medium, and the thickness (t) of the sheet being inspected.

(3) The method in the above (2), wherein when $Lp_1$ and $Lp_2$ ($Lp_1 < Lp_2$) are the values of L in which f(L) gives f(L)/f(Lp)=−3 dB, L is more than Lp1 and less than $Lp_2$.

(4) The method in the above (2), wherein the coupling medium is a liquid, and wherein Lp satisfies Lp=0.75(FT+FR)−{(CS/CW)−1}t.

(5) The method in the above (3), wherein the coupling medium is a liquid, and wherein Lp satisfies Lp=0.75(FT+FR)−{(CS/CW)−1}t.

(6) The method in the above (5), wherein $Lp_1$ and $Lp_2$ satisfy $Lp_1$=0.68(FT+FR)−{(CS/CW)−1}t, $Lp_2$=0.81(FT+FR)−{(CS/CW)−1}t, respectively.

(7) An ultrasonic flaw detecting instrument comprising: a line-focused ultrasonic transmitter transmitting ultrasonic waves into the sheet being inspected approximately in a perpendicular direction to the sheet through a coupling medium; a line-focused ultrasonic receiver receiving ultrasonic waves reflected at an internal flaw through the coupling medium; a receiving amplifier amplifying the received ultrasonic signals which have been transformed into electrical signals; a gating means for picking up amplified signals of the echo from the internal flaw; and a comparator detecting the signals of the echo from the internal flaw which is more than or equal to a predetermined threshold amplitude, wherein the transmitter and the receiver are arranged face to face with the sheet being inspected between them, and wherein the gap length (L) between the transmitter and the receiver is near the minimum value (Lp) in which the height (f(L)) of the echo from the internal flaw takes the maximum value.

(8) The instrument in the above (7), wherein Lp is determined by a focal length (FT) of the line-focused ultrasonic transmitter in the coupling medium, a focal length (FR) of the line-focused ultrasonic receiver in the coupling medium, the velocity (CS) of ultrasonic waves in the sheet being inspected, the velocity (CW) of ultrasonic waves in the coupling medium, and a thickness (t) of the sheet being inspected.

(9) The instrument in the above (8), wherein when $Lp_1$ and $Lp_2$ ($Lp_1 < Lp_2$) are the values of L in which f(L) gives $f(L)/f(Lp) = -3$ dB, L is more than $Lp_1$ and less than $Lp_2$.

(10) The instrument in the above (8), wherein the coupling medium is a liquid, and wherein Lp satisfies $Lp=0.75(FT+FR)-\{(CS/CW)-1\}t$.

(11) The instrument in the above (9), wherein the coupling medium is a liquid, and wherein Lp satisfies $Lp=0.75(FT+FR)-\{(CS/CW)-1\}t$.

(12) The instrument in the above (11), wherein $Lp_1$ and $Lp_2$ satisfy $Lp_1=0.68(FT+FR)-\{(CS/CW)-1\}t$, $Lp_2=0.81(FT+FR)-\{(CS/CW)-1\}t$, respectively.

(13) The instrument in any one of the above items (7) to (12), the line-focused ultrasonic transmitter and the line-focused ultrasonic receiver are linear probe arrays respectively.

Referring now to the drawings, the present invention will be described in detail.

FIG. 1 shows a basic configuration of the present invention. A line-focused ultrasonic transmitter 20 and a line-focused ultrasonic receiver 30 are arranged face to face with a rolled metallic sheet 10 being inspected between them. Coupling medium such as water exists between the line-focused ultrasonic transmitter 20 and the sheet 10 being inspected, and between the line-focused ultrasonic receiver 30 and the sheet 10 being inspected. As for the line-focused ultrasonic transmitter 20 and the line-focused ultrasonic receiver 30, a line-focused single-element probe or a line-focused linear (one-dimensional) probe array may be used. FIG. 2 illustrates positional relationship between the line-focused ultrasonic transmitter 20 and the sheet 10 being inspected, and between the line-focused ultrasonic receiver 30 and the sheet 10 being inspected. The focal length of a line-focused ultrasonic beam 21 transmitted from the line-focused ultrasonic transmitter 20 in a coupling medium is denoted as "FT" (mm). The focal length of a line-focused receiving beam 31 formed by the line-focused ultrasonic receiver 30 in a coupling medium is denoted as "FR" (mm). At this time, the gap length "L" (mm) between the line-focused ultrasonic transmitter 20 and the line-focused ultrasonic receiver 30 is set so as to satisfy the equation (1). This is the feature of the present invention.

$$0.68(FT+FR) \leq L+\{(CS/CW)-1\}t \leq 0.81(FT+FR) \qquad (1)$$

Provided that:
CS: the ultrasonic velocity in the rolled metallic sheet (m/sec),
CW: the ultrasonic velocity in the coupling medium (m/sec),
t: the thickness of the rolled metallic sheet (mm).

In Japanese Unexamined Patent Publication No. 7-253414, on the basis of an experimental result, when the focal length in the coupling medium of the line-focused beam transmitted from the ultrasonic transmitter is denoted as "F" (mm), the gap length "Ls" (mm) between the ultrasonic transmitter and the ultrasonic receiver is set so as to satisfy the equation (2). This is based on the result of the experiment in which, using the line-focused ultrasonic transmitter with the focal length "F"=38 mm and water as the coupling medium, heights of echoes from internal flaws are measured by changing "Ls" from 10 mm to 35 mm approximately.

$$Ls \leq F-\{(CS/CW)-1\}t+5.5 \qquad (2)$$

On the requirement of the equation (2), the contact accident of the sheet being inspected with the ultrasonic transmitter and the ultrasonic receiver cannot be avoided as described above.

Therefore, the inventors ardently studied the method and the instrument therefor to further increase the gap length between the ultrasonic transmitter and the ultrasonic receiver for preventing the contact accident. As a result of the study, it has been definitely shown by the present invention that the gap length between the ultrasonic transmitter and the ultrasonic receiver can be increased further, while moreover the echoes from internal flaws can be effectively received.

The experiment leading to the invention will be described.

With an instrument comprising a line-focused ultrasonic transmitter with a focal length in water "FT" being 38 mm, and a line-focused ultrasonic receiver with a focal length in water "FR" being 38 mm, the relationship between the height of the echo from an internal flaw and the gap length "L" between the line-focused ultrasonic transmitter and the line-focused ultrasonic receiver is surveyed, using water as the coupling medium. A steel sheet of 4.5 mm in thickness having an internal flaw of 50 μm in width and 100 μm in length is used as the sheet being inspected. The result thereof is shown in FIG. 3.

The height "f(L)" of the echo from the internal flaw decreases as "L" increases in the range of "L"≦35 mm. The "f(L)", however, rises quickly in the range of "L">35 mm to take the maximum value at "L"=43 mm, falls again thereafter. In the vicinity of the maximum value, the sufficient "f(L)" is secured.

The gap length "Lp" between the line-focused ultrasonic transmitter and the line-focused ultrasonic receiver in which the height "f(L)" of the echo from the internal flaw takes the maximum value is given by the equation (3).

$$Lp=0.75(FT+FR)-\{(CS/CW)-\}t \qquad (3)$$

Provided that;
FT: the focal length (mm) in the coupling medium of the line-focused beam transmitted by the line-focused ultrasonic transmitter,
FR: the focal length (mm) in the coupling medium of the line-focused beam formed by the line-focused ultrasonic receiver,
CS: the ultrasonic velocity (m/sec) in the sheet being inspected,
CW: the ultrasonic velocity (m/sec) in the coupling medium,
t: the thickness (mm) of the sheet being inspected.

This relationship has been found by the following experiment. Three kinds of line-focused ultrasonic transmitters and of line-focused ultrasonic receivers, each kind having the focal length "FT" or "FR" in the coupling medium of 38 mm, 57 mm, and 76 mm, respectively, are prepared. Using water as the coupling medium, under the combination shown in Table 1, the same experiment as described above has been carried out to obtain the gap length "Lp" at which the height of the echo from the internal flaw takes the maximum value. The result thereof is shown in FIG. 4. The horizontal axis represents the sum of the focal length "FT" of the line-focused ultrasonic transmitter and the focal length "FR" of the line-focused ultrasonic receiver (FT+FR). The sum (FT+FR) and the minimum value of the gap length "Lp" in which the height of the echo from the internal flaw takes the maximum value are linearly correlated and the slope thereof is 0.75. Accordingly, the minimum value of the gap length "Lp" in which the height of the echo from the internal flaw takes the maximum value can be given by the equation (4).

$$Lp = 0.75(FT+FR) + \alpha \text{ (provided that "}\alpha\text{" is a constant)} \quad (4)$$

The value of the constant "$\alpha$" has been studied as follows:

The value "$\alpha$" is obtained from FIG. 4 to be approximately $-13.4$ (mm). It is estimated that the focal lengths "FT" and "FR" are observed to be reduced by refraction of the beam, when the sheet being inspected is located within the transmitting line-focused beam and the receiving line-focused beam. This effect can be expressed by obtaining the value "$\alpha$" from the equation (5).

$$\alpha = -\{(CS/CW) - 1\}t \quad (5)$$

CS=5950 m/sec for the steel sheet, CW=1500 m/sec for water at room temperature, and the steel sheet thickness for the experiment is 4.5 mm. Using these values, the right side of the equation (5) is calculated to obtain the value of $-13.35$ (mm), which quite coincides with the experimental result.

Therefore, the minimum value of the gap length "Lp" in which the height of the echo from the internal flaw takes the maximum value can be arranged to be the equation (3).

Practically, if the echo height is within $-3$ dB with reference to the maximum value flaw detection with sufficient signal to noise ratio can be achieved. Based on this value, allowable range of the gap length "L" are obtained. From FIG. 3, the range of the gap length "L" in which the echo height is within $-3$ dB with reference to the maximum value is obtained to be 38 to 48 mm.

As described above, the relationship between the height of the echo from the internal flaw and the gap length "L" depends on the focal length "FT" in the coupling medium of the line-focused beam transmitted by the line-focused ultrasonic transmitter and the focal length "FR" in the coupling medium of the line-focused beam formed by the line-focused ultrasonic receiver. Therefore, the allowable range of the gap length "L" can be also given by multiplying the sum of the focal length "FT" of the line-focused ultrasonic transmitter and the focal length "FR" of the line-focused ultrasonic receiver (FT+FR) by a coefficient.

The minimum of the allowable range of "L" is defined by "$Lp_1$", while the maximum is represented by "$Lp_2$". Provided that "$Lp_1$"=38 mm, the coefficient is calculated to be 0.68, and if "$Lp_2$"=48 mm, the coefficient is calculated to be 0.81. Therefore, $Lp_1$ and $Lp_2$ can be given by the following equation.

$$Lp_1 = 0.68(FT+FR) - \{(CS/CW) - 1\}t$$

$$Lp_2 = 0.81(FT+FR) - \{(CS/CW) - 1\}t$$

Accordingly, the allowable range of the gap length "L" can be given as follows.

$$0.68(FT+FR) \leq L + \{(CS/CW) - 1\}t \leq 0.81(FT+FR)$$

BEST MODE FOR CARRYING OUT THE INVENTION

Figure 1:
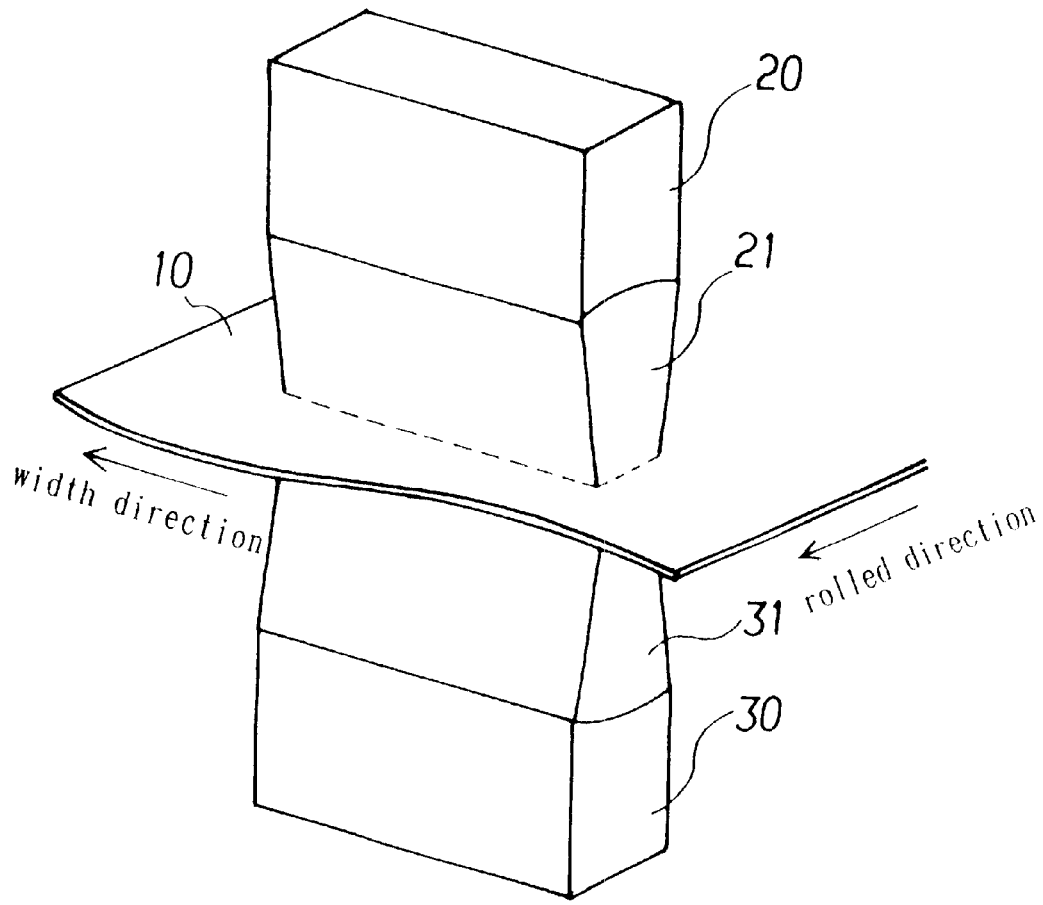
FIG. 1 is a basic conceptual view showing the relationship between the rolled direction of the sheet being inspected and the line direction of the line-focused beam in the present invention.
Figure 2:
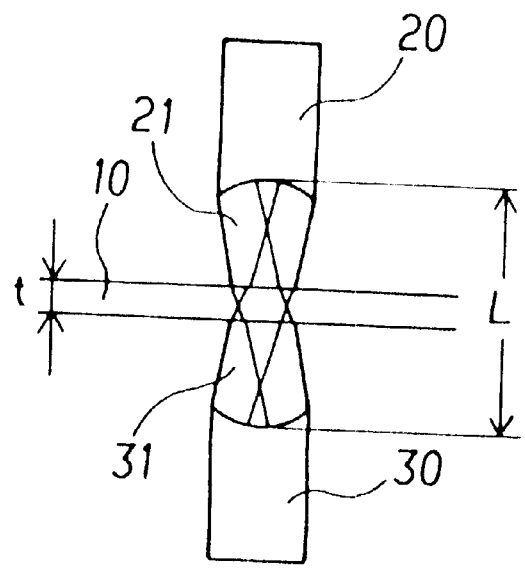
FIG. 2 is a schematic view showing the constitution in which a line-focused ultrasonic transmitter and a line-focused ultrasonic receiver are arranged face to face with a sheet being inspected between them.
Figure 3:
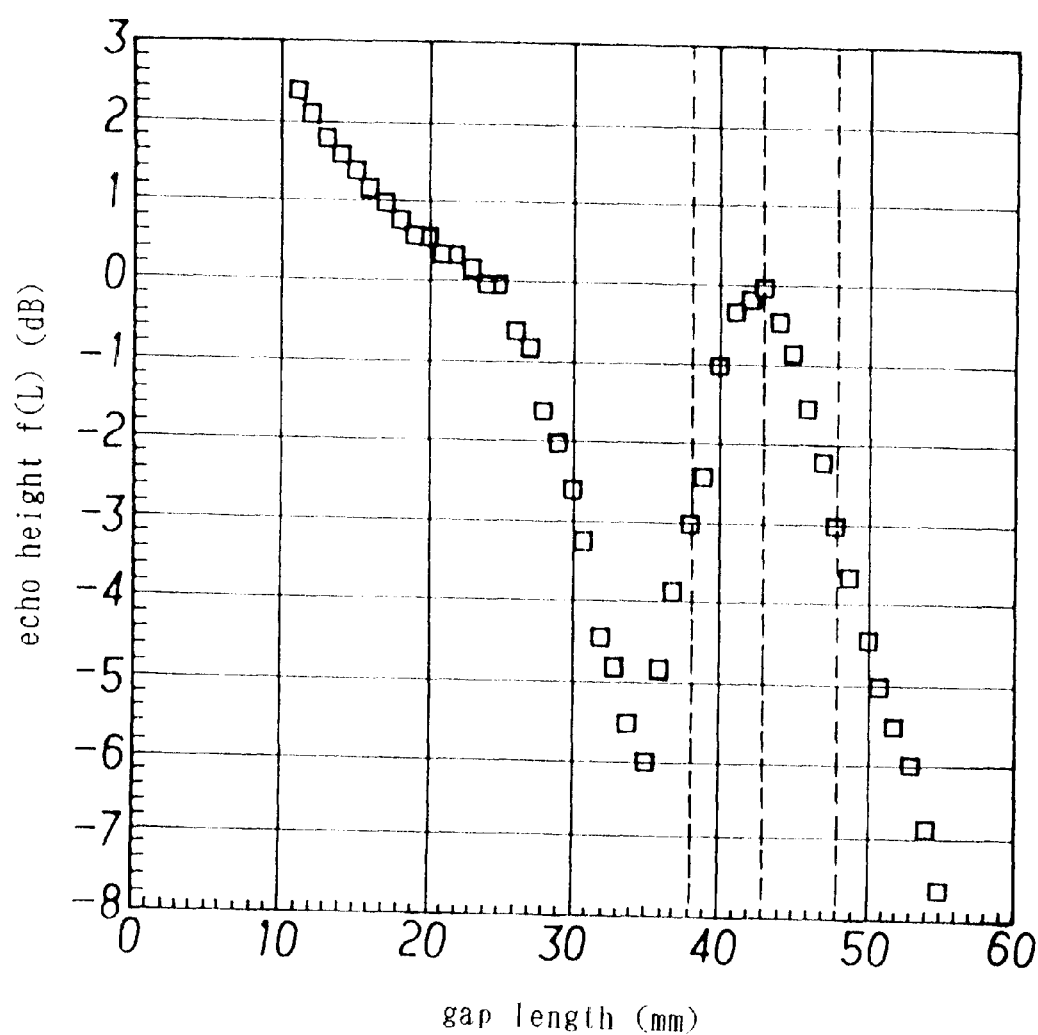
FIG. 3 is a graph of the experimental result showing the relationship between the gap length between two probes and the height of the echo from an internal flaw.
Figure 4:
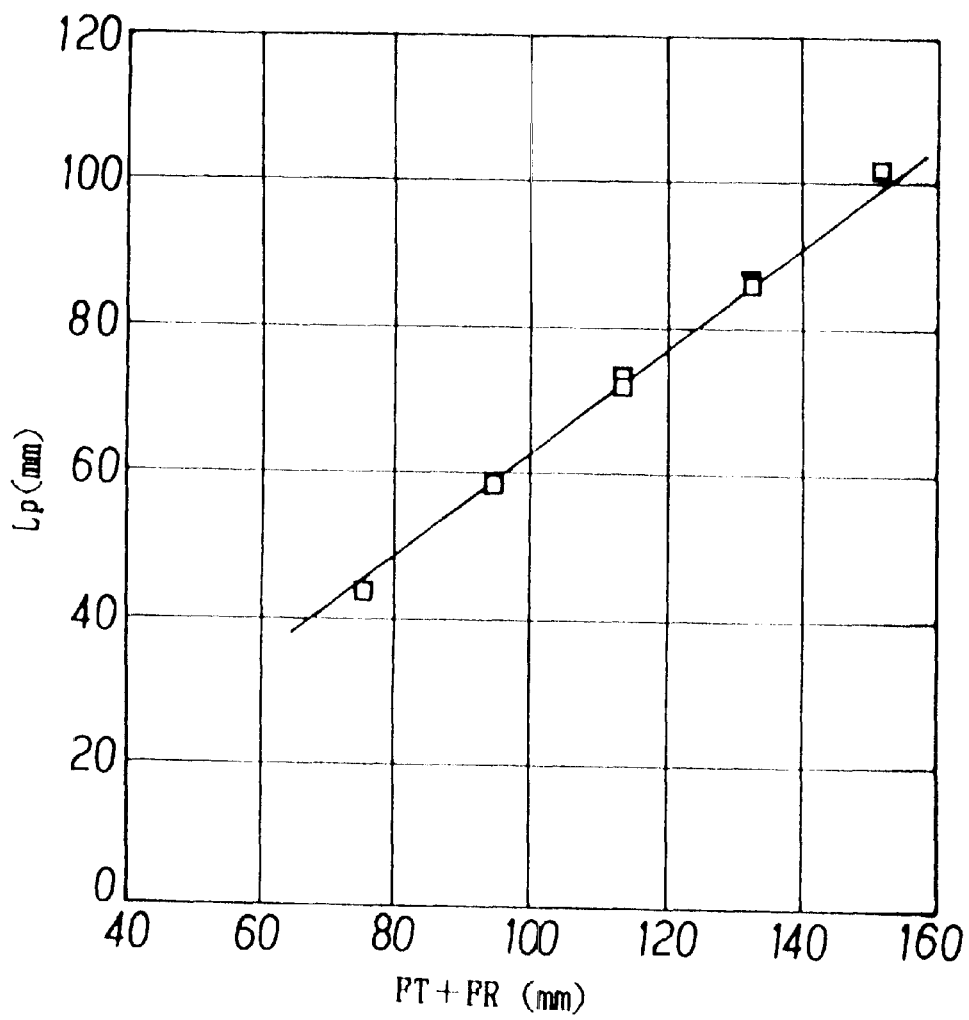
FIG. 4 is a graph of an experimental result showing the relationship between the sum of the focal lengths in the coupling medium of the two probes and the maximum value of the height of the echo from a flaw.
Figure 5:
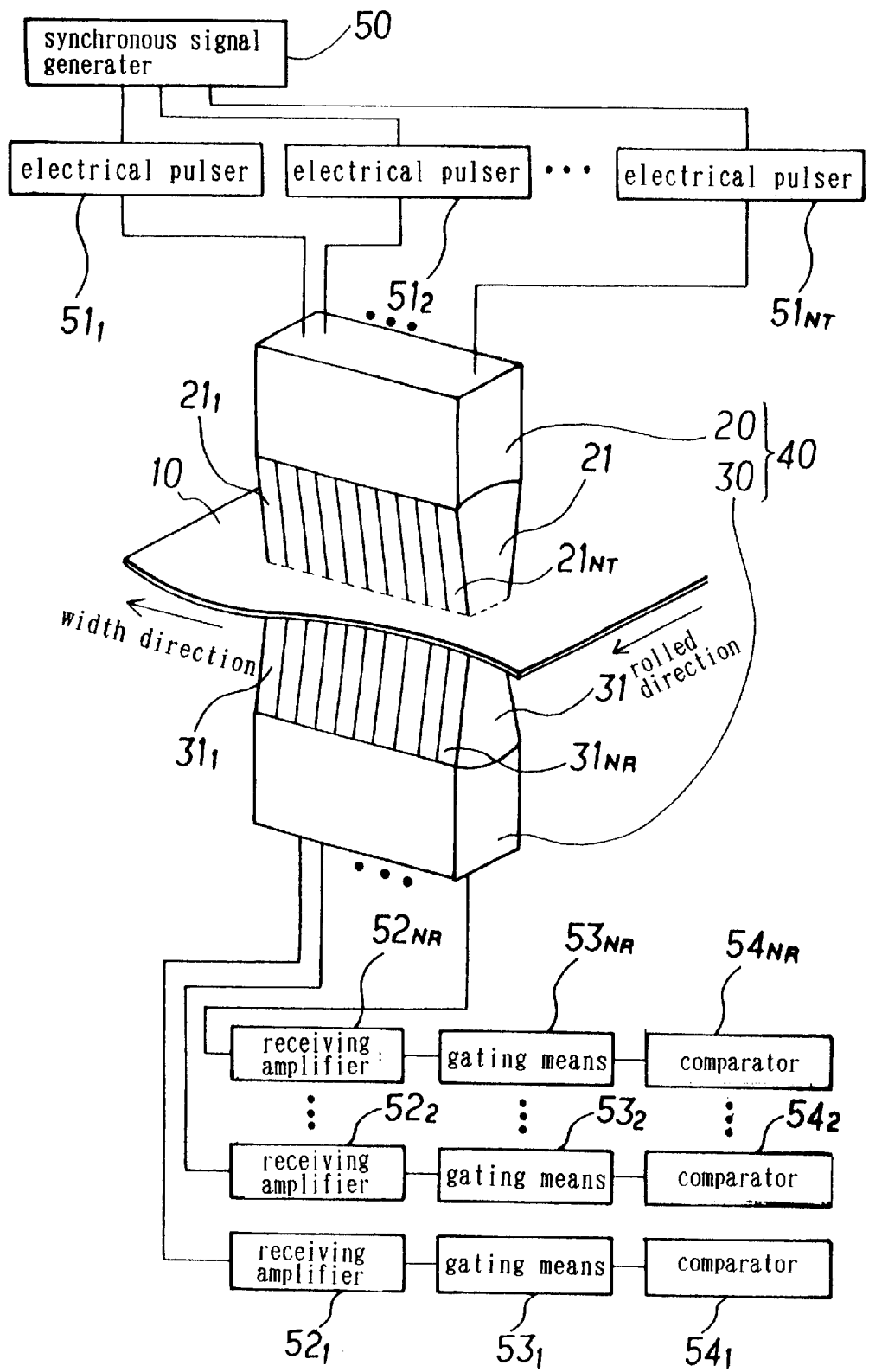
FIG. 5 is a conceptual view showing a configuration of an ultrasonic flaw detection instrument of the present invention.

Referring to FIG. 5, an embodiment of the present invention will be described in detail. A line-focused ultrasonic transmitter 20 and a line-focused ultrasonic receiver 30 are arranged face to face with a steel sheet being inspected (a sheet 10 being inspected, which will be referred to a steel sheet 10) between them. As for a coupling medium between the line-focused ultrasonic transmitter 20 and the steel sheet 10, and between the line-focused ultrasonic receiver 30 and the steel sheet 10, water is used. The gap length "L" between the line-focused ultrasonic transmitter 20 and the line-focused ultrasonic receiver 30 is set so as to satisfy the following equation (1).

$$0.68(FT+FR) \leq -L + \{(CS/CW) - 1\}t \leq 0.81(FT+FR) \quad (1)$$

Both of the line-focused ultrasonic transmitter 20 and the line-focused ultrasonic receiver 30 are line-focused linear prove arrays. The line-focused ultrasonic transmitter 20 and the line-focused ultrasonic receiver 30 are referred to a probe pair 40 hereafter. In addition, the number of elements of the line-focused ultrasonic transmitter 20 which is a line-focused linear (one-dimensional) probe array is referred to "NT" (being 10 herein), while the number of the elements of the line-focused ultrasonic receiver 30 which is a line-focused linear (one-dimensional) probe array is referred to "NR" (being 10 herein).

The probe pairs 40 are arranged in the width direction of the steel sheet 10 such that the whole width of the steel sheet 10 is inspected with the probe pairs 40 for the purpose of continuous flaw detection of the entire volume of the steel sheet 10. Electrical pulsers $51_1$ to $51_{NT}$ of the same number as the number of elements "NT" are connected to every each element of the line-focused ultrasonic transmitter 20. One or a plurality of synchronous signal generators 50 (one in FIG. 5) are connected to the electrical pulsers $51_1$ to $51_{NT}$. The synchronous signal generator 50 generates clock pulses so that all or a plurality of the electrical pursers $51_1$ to $51_{NT}$ generate electrical pulses simultaneously (all simultaneously in FIG. 5). Electrical pulses are simultaneously generated from all or a plurality of the electrical pulsers $51_1$ to $51_{NT}$ (all simultaneously in FIG. 5) which receive clock pulses from the synchronous signal generator 50. The electrical pulses are applied to each element of the line-focused ultrasonic transmitter 20, so that line-focused ultrasonic beams 21i to 21NT are transmitted from each element of the line-focused ultrasonic transmitter 20 (transmitted simultaneously from all elements in FIG. 5). When the transmitted line-focused ultrasonic beams $21_1$ to $21_{NT}$ travel through water to reach the surface of the steel sheet 10, the beams propagate into the steel sheet 10 approximately in a thickness direction of the sheet. If an internal flaw exists in the beam path, parts of the line-focused ultrasonic beams $21_1$ to $21_{NT}$ are thereby reflected. The reflected ultrasound, which is reflected once again at the top or back surface of the steel sheet 10, travels through water after passing through the steel sheet 10 to be caught by line-focused receiving beams $31_1$ to $31_{NR}$ formed by the line-focused ultrasonic receiver 30, resulting in being received by the line-focused ultrasonic receiver 30. The element that receives the echo from the internal flaw in the line-focused ultrasonic receiver 30 depends on the location of the internal flaw in the width direction of the steel sheet 10. The echo from the internal flaw received by the line-focused ultrasonic receiver 30 is transformed into the electrical signal to be amplified by receiving amplifiers $52_1$ to $52_{NR}$. Only the signal of the echo from the internal flaw is picked up by gating means $53_1$ to $53_{NR}$ to be fed to comparators $54_1$ to $54_{NR}$. When the signal more than a predetermined threshold amplitude is input therein, the comparators $54_1$ to $54_{NR}$ output the electrical pulse which indicates the presence of the internal flaw.

Figure 6:
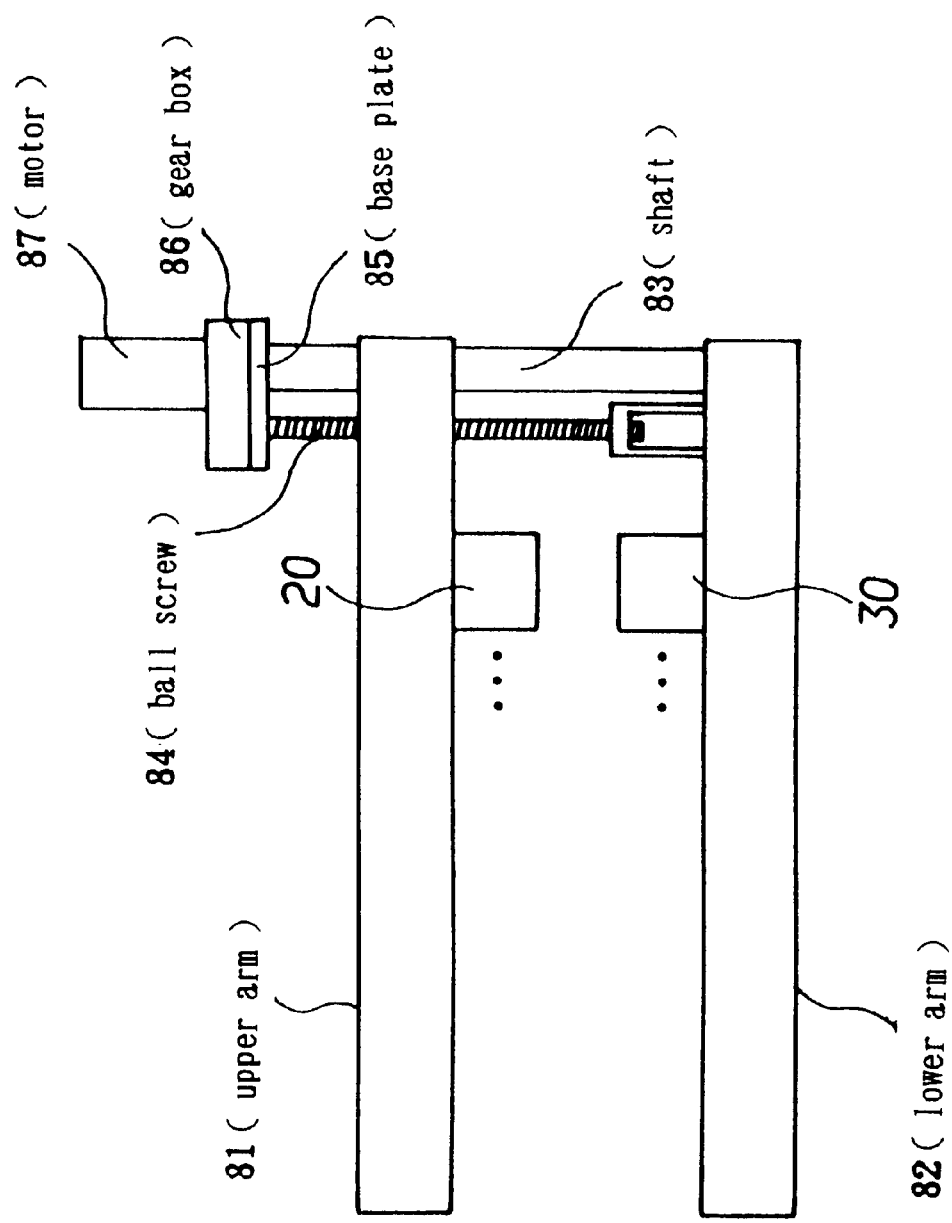
FIG. 6 is a schematic view showing an example of means for setting the gap distance between the transmitting probes and the receiving proves.

Gap length setting means applied to the present invention can be formed by employing a conventionally known technique, and an example thereof is shown in FIG. 6. FIG. 6 illustrates an example in which the gap length "L" is adjusted within the above-mentioned range by changing the position of the line-focused ultrasonic transmitter 20, while the position of the line-focused ultrasonic receiver 30 is fixed. An upper arm 81 mounting the line-focused ultrasonic transmitter 20 thereon is driven in the vertical direction by the rotation of a ball screw 84 rotated by the power of a motor 87 through gear-shifting by gears (omitted in the drawing) in a gear box 86. Although the line-focused ultrasonic transmitter 20 and the line-focused ultrasonic receiver 30 are illustrated as being only one for each for preventing complicatedness of the drawing, they are disposed such that the required number are arranged without a gap in the width direction of a steel sheet 10. A lower arm 82, a shaft 83, and a base sheet 85 are fixed, while the upper arm is slidable relative to the shaft 83.

Differently, another configuration, such as a structure in which the lower arm position is changeable or a structure in which both positions of the lower and upper arms are adjustable, may be adopted, and any of them can be formed by conventionally known means. On the other side surfaces (opposite sides to the shaft 83) of the upper and lower arms 81, 82, guiding means such as a shaft may be also formed.

Figure 7:
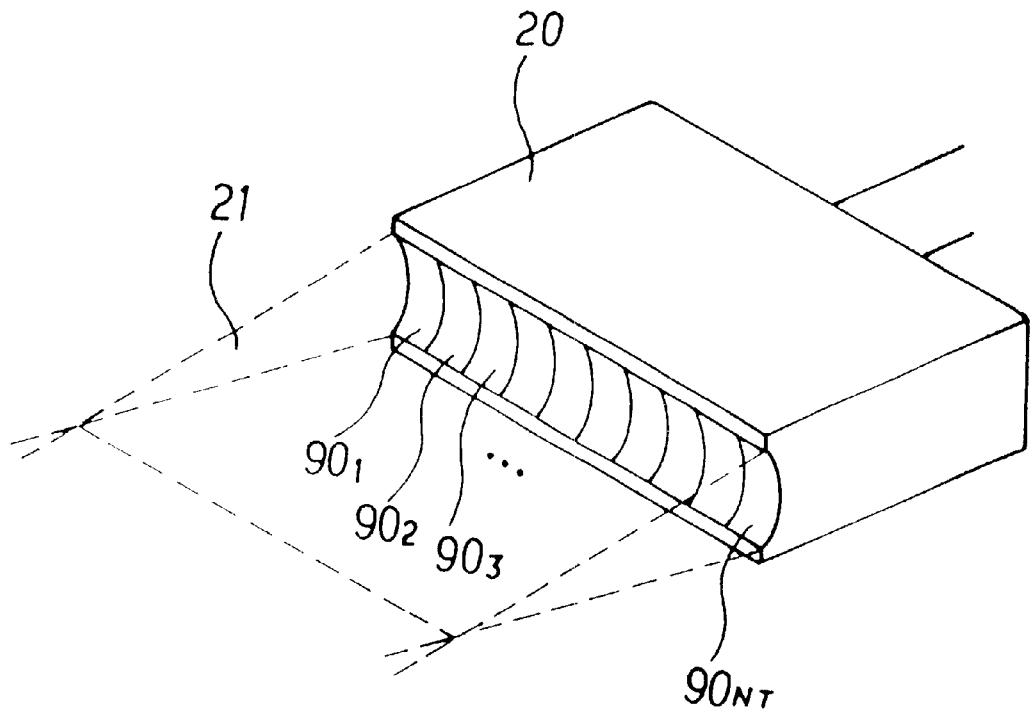
FIG. 7 is a schematic view showing a configuration of a line-focused ultrasonic transmitter.

FIG. 7 illustrates a configuration of the line-focused ultrasonic transmitter 20, which is a line-focused linear (one-dimensional) probe array. NT pieces of piezoelectric elements $90_1$ to $90_{NT}$ are closely arranged with each other in the width direction, and moreover the surface of each element is formed in a cylindrical-concave surface. Accordingly, a line-focused ultrasonic beam that is linearly focused is transmitted. While line-focused ultrasonic beams $21_1$ to $21_{NT}$ are transmitted by each of elements (not shown), as a whole the line-focused ultrasonic beam 21 is formed. In addition, the width of the piezoelectric elements $90_1$ to $90_{NT}$ (the width in the arrangement direction of the elements) may preferably be 2.0 to 15 mm as disclosed in Japanese Unexamined Patent Publication No. 7-253414. In this manner, the line-focused ultrasonic transmitter 20, which is a line-focused linear (one-dimensional) probe array, can be formed.

Figure 8:
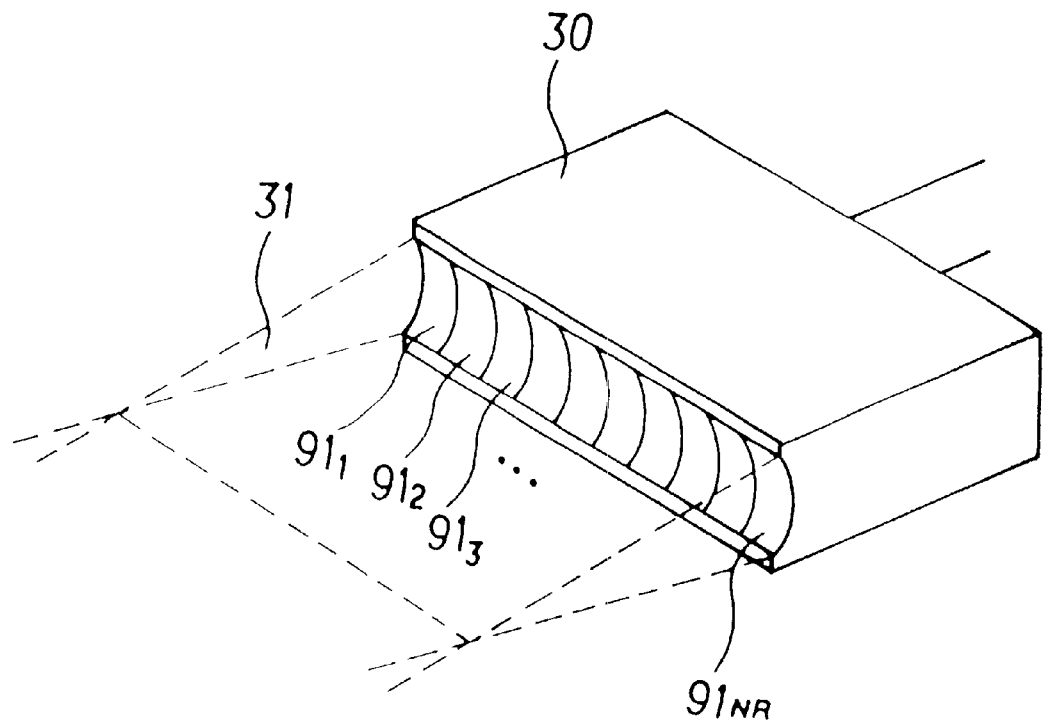
FIG. 8 is a schematic view showing a configuration of a line-focused ultrasonic receiver.

FIG. 8 illustrates a configuration of the line-focused ultrasonic receiver 30, which is a line-focused linear (one-dimensional) probe array. The description in detail of this configuration is omitted because it is similar to the line-focused ultrasonic transmitter 20. In addition, the width of the piezoelectric elements $91_1$ to $91_{NR}$ (the width in the arrangement direction of the elements) may preferably be more than 1.0 mm as disclosed in Japanese Unexamined Patent Publication No. 7-253414. In this manner, the line-focused ultrasonic receiver 30, which is a line-focused linear (one-dimensional) probe array, can be formed.

Using the ultrasonic flaw detection instrument according to the present invention, the flaw detection of a steel sheet of 2.0 mm in thickness, 1000 mm in width is conducted.

The number of elements of the line-focused ultrasonic transmitter 20 which is a line-focused linear (one-dimensional) probe array is set at 10, and the width of the line-focused ultrasonic beam transmitted by each element is to be 6 mm. The number of elements of the line-focused ultrasonic receiver 30 which is a line-focused linear (one-dimensional) probe array is set at 10, and the width of a line-focused receiving beam formed by each element is to be 6 mm. The flaw detection of a linear region of 60 mm in length can be conducted by one of the probe pair 40. That is, the flaw detection of the steel sheet of 1000 mm in width can be conducted by only 17 pairs of the probe pairs 40.

Moreover, the gap length between the transmitting probes and the receiving probes can be set at 51 mm, which is larger by 13.5 mm than the gap length of 37.5 mm based on Japanese Unexamined Patent Publication No. 7-253414.

When the instrument based on the present invention has been continuously operated in on-line inspection for one month, no contact of a wavy steel sheet with the probe pair 40 could be found. For reference purposes, when the instrument based on Japanese Unexamined Patent Publication No. 7-253414 was operated at the gap length of 37.5 mm several times of contact a month were confirmed.

Industrial Applicability

By use of the present invention, the gap length between the line-focused ultrasonic transmitter and the line-focused ultrasonic receiver can be increased relative to a conventional art. Therefore, when a sheet being inspected having a wavy shape is passed through in on-line inspection, it does not contact with the transmitter and the receiver to be not scratched thereon, resulting in increasing the useful life of the probe pair. That is, by use of the present invention, continuous flaw detection of extremely microscopic internal flaws in a steel sheet can be reliably achieved with maintenance-free performance.

TABLE 1

|      | No. 1 | No. 2 | No. 3 | No. 4 | No. 5 | No. 6 |
|------|-------|-------|-------|-------|-------|-------|
| FT   | 38    | 38    | 38    | 57    | 57    | 76    |
| FR   | 38    | 57    | 76    | 57    | 76    | 76    |
| FT + FR | 76 | 95    | 114   | 114   | 133   | 152   |

(unit: mm)

What is claimed is:

1. An ultrasonic flaw detection method comprising the steps of: transmitting ultrasonic waves into a sheet being inspected approximately in a perpendicular direction to the sheet through a coupling medium with a line-focused ultrasonic transmitter; receiving ultrasonic waves reflected at an internal flaw through the coupling medium with a line-focused ultrasonic receiver; amplifying the received ultrasonic signals which have been transformed into electrical signals; picking up amplified signals of the echo from the internal flaw; and detecting the flaw by detecting a signal more than a predetermined threshold amplitude, wherein the transmitter and the receiver are arranged face to face with the sheet being inspected between them, and wherein a gap length (L) between the transmitter and the receiver is near a minimum value (Lp) in which the height (f(L))of the echo from the internal flaw takes a maximum value.

2. The method according to claim 1, wherein Lp is determined by a focal length (FT) of the line-focused ultrasonic transmitter in the coupling medium, a focal length (FR) of the line-focused ultrasonic receiver in the coupling medium, the velocity (CS) of ultrasonic waves in the sheet being inspected, the velocity (CW) of ultrasonic waves in the coupling medium, and a thickness (t) of the sheet being inspected.

3. The method according to claim 2, wherein when $Lp_1$ and $Lp_2$ ($Lp_1 < Lp_2$) are the values of L in which f(L) gives f(L)/f(Lp)=−3 dB, L is more than $Lp_1$ and less than $Lp_2$.

4. The method according to claim 2, wherein the coupling medium is a liquid, and wherein Lp satisfies Lp=0.75(FT+FR)−{(CS/CW)−1}t.

5. The method according to claim 3, wherein the coupling medium is a liquid, and wherein Lp satisfies Lp=0.75(FT+FR)−{(CS/CW)−1}t.

6. The method according to claim 5, wherein $Lp_1$ and $Lp_2$ satisfy $Lp_1$=0.68(FT+FR)−{(CS/CW)−1}t, $Lp_2$=0.81(FT+FR)−{(CS/CW)−1}t, respectively.

7. An ultrasonic flaw detecting instrument comprising: a line-focused ultrasonic transmitter transmitting ultrasonic waves into a sheet being inspected approximately in a perpendicular direction to the sheet through a coupling medium; a line-focused ultrasonic receiver receiving ultrasonic waves reflected at an internal flaw through the coupling medium; a receiving amplifier amplifying the received ultrasonic signals which have been transformed into electrical signals; gating means for picking up amplified signals of an echo from the internal flaw; and a comparator detecting the signals of the echo from the internal flaw which is more than or equal to a predetermined threshold amplitude, wherein the transmitter and the receiver are arranged face to face with the sheet being inspected between them, and wherein a gap length (L) between the transmitter and the receiver is near a minimum value (Lp) in which the height (f(L)) of the echo from the internal flaw takes a maximum value.

8. The instrument according to claim 7, wherein Lp is determined by a focal length (FT) of said line-focused ultrasonic transmitter in the coupling medium, a focal length (FR) of said line-focused ultrasonic receiver in the coupling medium, the velocity (CS) of ultrasonic waves in the sheet being inspected, the velocity (CW) of ultrasonic waves in the coupling medium, and a thickness (t) of the sheet being inspected.

9. The instrument according to claim 8, wherein the coupling medium is a liquid, and wherein Lp satisfies Lp=0.75(FT+FR)−{(CS/CW)−1}t.

10. The instrument according to claim 9, said line-focused ultrasonic transmitter and said line-focused ultrasonic receiver are linear probe arrays, respectively.

11. The instrument according to claim 8, wherein when $Lp_1$ and $Lp_2$ ($Lp_1 < Lp_2$) are the values of L in which f(L) gives f(L)/f(Lp)=−3 dB, L is more than $Lp_1$ and less than $Lp_2$.

12. The instrument according to claim 11, wherein the coupling medium is a liquid, and wherein Lp satisfies Lp=0.75(FT+FR)−{(CS/CW)−1}t.

13. The instrument according to claim 12, wherein $Lp_1$ and $Lp_2$ satisfy $Lp_1$=0.68(FT+FR)−{(CS/CW)−1}t, $Lp_2$=0.81(FT+FR)−{(CS/CW)−1}t, respectively.

14. The instrument according to claim 13, said line-focused ultrasonic transmitter and said line-focused ultrasonic receiver are linear probe arrays, respectively.

15. The instrument according to claim 12, said line-focused ultrasonic transmitter and said line-focused ultrasonic receiver are linear probe arrays, respectively.

16. The instrument according to claim 11, said line-focused ultrasonic transmitter and said line-focused ultrasonic receiver are linear probe arrays, respectively.

17. The instrument according to claim 8, said line-focused ultrasonic transmitter and said line-focused ultrasonic receiver are linear probe arrays, respectively.

18. The instrument according to claim 7, said line-focused ultrasonic transmitter and said line-focused ultrasonic receiver are linear probe arrays, respectively.

* * * * *